United States Patent [19]

DeCote, Jr.

[11] Patent Number: 4,708,142
[45] Date of Patent: Nov. 24, 1987

[54] AUTOMATIC CARDIAC CAPTURE THRESHOLD DETERMINATION SYSTEM AND METHOD

[75] Inventor: Robert DeCote, Jr., Miami Beach, Fla.

[73] Assignee: Cordis Corporation, Miami, Fla.

[21] Appl. No.: 738,609

[22] Filed: May 28, 1985

[51] Int. Cl.[4] ............................................... A61N 1/36
[52] U.S. Cl. ............................................. 128/419 PT
[58] Field of Search ................... 128/419 PG, 419 PT

[56] References Cited

U.S. PATENT DOCUMENTS

| | | | |
|---|---|---|---|
| 3,683,934 | 8/1972 | Bukowiecki et al. | 128/419 PG |
| 3,757,790 | 9/1973 | Herrmann | 128/419 PT |
| 3,777,762 | 12/1973 | Nielsen | 128/419 PT |
| 3,800,801 | 4/1974 | Gaillard | 128/419 PT |
| 3,949,758 | 4/1976 | Jirak | 128/419 PG |
| 4,245,643 | 1/1981 | Benzing, III et al. | 128/419 PT |
| 4,290,430 | 9/1981 | Bihn et al. | 128/419 PT |
| 4,337,776 | 7/1982 | Daly et al. | 128/419 PT |

OTHER PUBLICATIONS

A New Electronic System for the Detection of the Stimulated Cardiac Response, J. Mugica, B. Lazarus, D. Delle-Vedove, Y. Lallemand, O. Hubert.

Primary Examiner—William E. Kamm
Attorney, Agent, or Firm—Lockwood, Alex, FitzGibbon & Cummings

[57] ABSTRACT

An automatic capture threshold determination system and method apply pacing pulses to a patient's heart while simultaneously monitoring intracardiac electrical activity to detect evoked cardiac contractions. The system and method automatically adjust the energy of the applied pacing pulses in accordance with a prearranged routine, until capture is obtained, thereby determining the minimum pulse amplitude required to reliably stimulate the heart.

11 Claims, 5 Drawing Figures

AUTOMATIC CARDIAC CAPTURE THRESHOLD DETERMINATION SYSTEM AND METHOD

BACKGROUND OF THE INVENTION

The present invention relates generally to a method and apparatus for assisting in matching a pacer to a patient's heart, and more particularly to a system and method for automatically determining the minimum pacing pulse amplitude required to reliably stimulate cardiac contractions. The system and method are particularly well adapted for use in a pacer system analyzer, wherein the operation of a pacer is monitored in association with a patient's heart prior to implantation.

To assist physicians in treating cardiac disorders of the type for which the use of implantable cardiac pacers is indicated, pacer system analyzers (PSA's) have been developed. These devices are used at the time of pacer implantation to measure the parameters of a pacer system, which includes the patient's heart, the pacer to be implanted, and the previously implanted pacer leads, without the need to perform separate procedures requiring multiple interconnections and an undesirably long time to complete. Pacers to be implanted are tested for proper programming and operation, not only while connected in a simulated pacing system environment, but also while connected to the actual system in which they are to be used. Moreover, pacer system analyzers are preferably equipped to generate pacing pulses as required to support the patient during the pacer implantation process, independently of the pacer to be implanted.

By using a pacer system analyzer prior to implantation of a pacer, a physician is able to program the operating parameters of the pacer system as required to suit the specific needs of an individual patient before the pacer has been fully implanted and the implantation surgery completed. This minimizes the likelihood for inconvenient, costly, and potentially injurious explantation of the pacer and/or its associated pacer leads.

One important parameter of a pacer system is capture threshold, which represents the minimum pacer output energy level required to reliably stimulate cardiac contractions. This is typically determined by varying the strength and duration characteristics of applied pacing pulses while simultaneously monitoring intracardiac electrical impulses produced during each contraction of the patient's heart. Capture is indicated when each applied pacing pulse consistently results in the occurrence of a heart contraction.

Previously, the determination of capture threshold involved a relatively complex and time consuming procedure. A pacer system analyzer, having an adjustable internal pacer circuit, was first coupled to the heart through a conventional cardiac lead, and the pacing rate was adjusted to be above the patient's intrinsic rate. Then, the pulse energy was manually adjusted by the cardiologist. A monitoring device coupled to the lead provided a visual "sense" indication upon the occurrence of each naturally occuring cardiac contraction. Consistently induced contractions did not result in the production of the visual "sense" indication since the presence of substantial lead recovery artifacts made it necessary to design the monitoring device to be insensitive for a specified refractory period following each applied pacing pulse. Capture was indirectly presumed when the "sense" visual display ceased entirely, indicating that contractions were presumably occurring synchronously during the monitoring device's post-pulse refractory period.

In prior systems, such an indirect capture detection method was mandated by the presence of the post-pulse lead recovery artifacts, which result from depolarization of the interface between the pacer lead and cardiac tissue and which typically exceeds the level of evoked cardiac response signals by several orders of magnitude.

One prior technique for directly detecting cardiac response signals involved applying a post pacing pulse reverse current to the lead in order to more rapidly depolarize the lead-cardiac interface. This technique found application as a palliative, but as an "exact" lead depolarization technique suffered from the fact that the unequal charge-discharge time constants were non-linear functions of pacer drive level, lead type, lead geometry, and timemodulated lead impedance. In addition, owing to the anodic voltages required, this approach introduced the possibility of inducing lead deterioration through corrosion.

Another prior technique was based on the observation that lead recovery artifacts correspond generally to the exponential decay characteristics of a resistor-capacitor network, and involved computing the anti-log of the post-pulse signal to recover the induced cardiac response. The accuracy of this system was inherently limited by the degree to which lead recovery artifacts departed from simple exponentials.

The present invention is directed to a system for automatically measuring a patient's cardiac capture threshold. The measurement steps, including variation of generated pulse energy levels and detection of cardiac capture, are performed automatically, thereby improving accuracy and repeatability while saving operating-room time and reducing complexity. The system can be used with any cardiac lead configuration such as unipolar, bipolar, tripolar, etc., with any of the currently used lead materials such as platinum, elgiloy, etc., and with any of the lead tip geometries such as screw-in, ball-tip, parabolic, etc.

In view of the foregoing, it is a general object of the present invention to provide a new and improved system and method for determining the capture threshold of a patient's heart.

It is a further object of the present invention to provide a system and method for measuring capture threhsold in which the measurement is performed automatically.

It is still another object of the present invention to provide an automatic capture threshold determining system and method which directly detects induced cardiac responses.

SUMMARY OF THE INVENTION

A cardiac capture threshold determination system is provided for automatically determining the minimum pacing pulse energy required to reliably stimulate contractions of a patient's heart. The system includes a pulse generator for developing pacing pulses of variable pulse energy for application to the heart, and a capture detection circuit coupled to the heart for detecting cardiac contractions stimulated in response to the applied pacing pulses. A pulse energy control, coupled to the pulse generator and responsive to the capture detection circuit, varies the pulse energy level such that the pulse energy increases when the capture detection circuit fails to detect cardiac contractions and decreases the pulse energy when the capture detection circuit detects cardiac contractions. A control circuit is coupled to the capture detection circuit and determines the cardiac capture threshold when the pulse energy is such that any incremental decrease therein will result in less than 100% reliable stimulation of cardiac contractions.

BRIEF DESCRIPTION OF THE DRAWINGS

The features of the present invention which are believed to be novel are set forth with particularity in the appended claims. The invention, together with the further objects and advantages thereof, may best be understood by reference to the following description taken in conjunction with the accompanying drawings, in the several figures of which like reference numerals identify like elements, and in which:

DESCRIPTION OF THE PREFERRED EMBODIMENT

Figure 1:
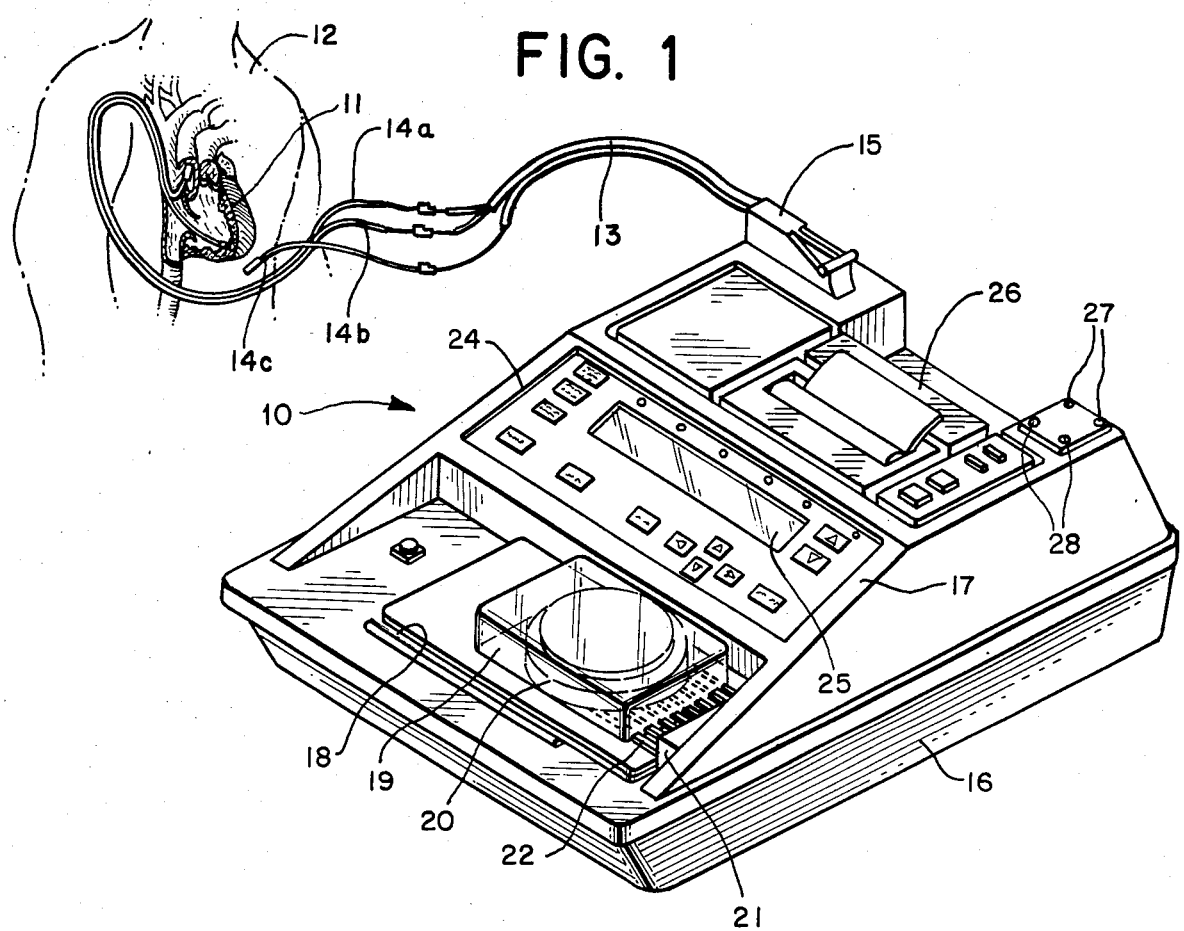
FIG. 1 is a perspective view of a pacer system analyzer incorporating an automatic capture threshold determination system constructed in accordance with the invention.

Referring to the figures, and particularly to FIG. 1, a pacer system analyzer (PSA) 10 is shown which incorporates an automatic capture threshold determination system constructed in accordance with the present invention. As illustrated, the PSA is connected to the heart 11 of a patient 12 by means of a patient cable assembly 13 which is connected at one end to the ends of a pair of unipolar atrial and ventricular pacing leads 14a and 14b, and a reference lead 14c each of which may be conventional in construction and operation. Alternately, bipolar pacing leads can be used where appropriate. The remaining end of the patient cable assembly is electrically connected to PSA 10 by means of a molded multicontact connector 15.

PSA 10 is contained within a generally rectangular housing 16 formed of a durable, insulating, plastic or like material and includes a sloping, generally flat, control panel 17. A portion of the housing is formed to provide a guide 18 for receiving a sealed package 19 containing a sterile implantable cardiac pacer 20. A connector 21 engages a plurality of electrical contacts 22 formed on package 19 to provide electrical communication between PSA 10 and implantable pacer 20.

Panel 17 includes a user keyboard 24 having a plurality of pressure sensitive user-actuable push button controls and a liquid crystal display (LCD) 25. PSA 10 operates in one of several user-selected modes in accordance with key stroke commands entered on keyboard 24. To assist the user in selecting the appropriate operating mode, a series of internally generated instructions and a plurality of measured pacer system operating parameters are displayed on LCD 25. A printer/plotter mechanism 26 provides a printed record of measured pacer system operating parameters and measured patient parameters, while two pairs of EGM electrodes 27 and 28 provide electrically isolated atrial and ventricular electrogram signals for connection to external instrumentation.

Heart 11, patient cable 13, leads 14a, 14b and 14c and pacer 20 together form a pacer system. PSA 10 functions to automatically measure various parameters of this system and to thereby assist a physician in selecting, programming, testing and implanting the pacer system components for maximum patient effectiveness. Additionally, proper operation of the entire pacing system can be verified before final implantation, and pacing pulses for supporting the patient during pacer implantation can be generated.

Figure 2:
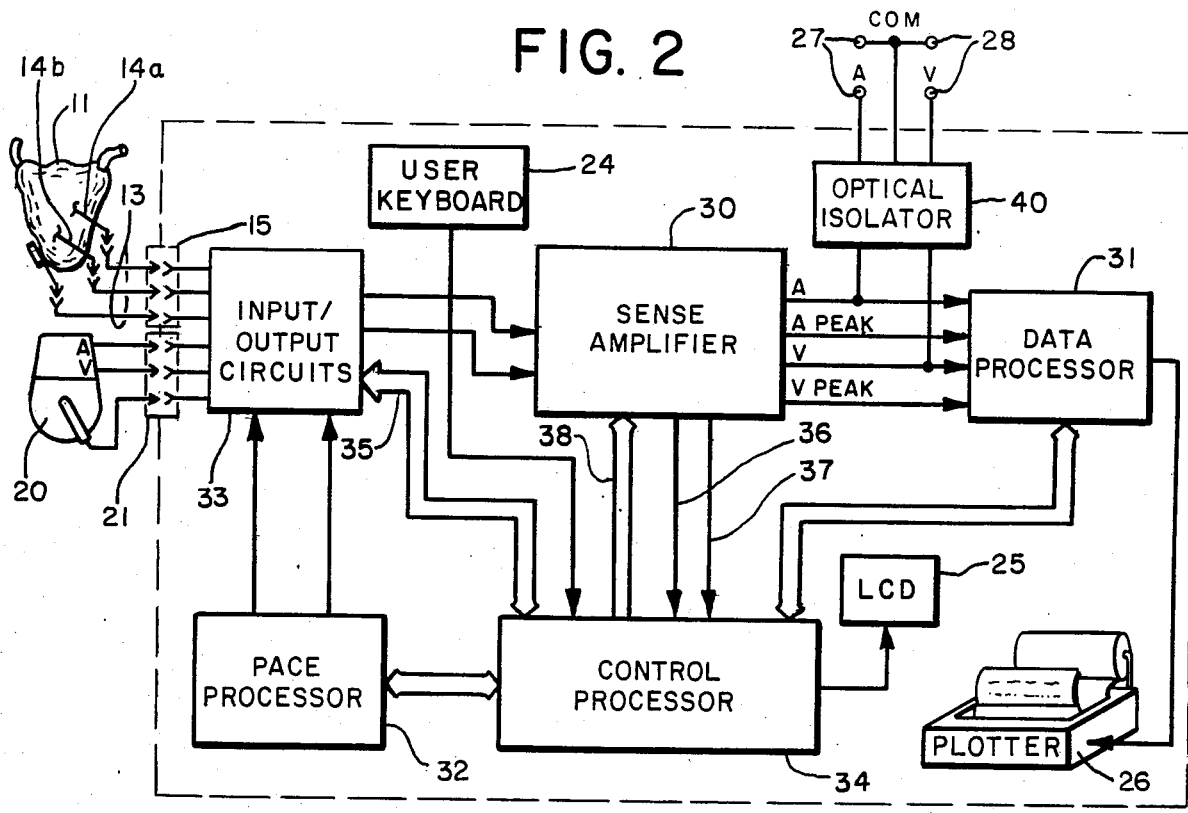
FIG. 2 is a simplified functional block diagram of the pacer system analyzer illustrated in FIG. 1 showing the principal subsystems thereof.

Referring to the simplified PSA system functional block diagram of FIG. 2, PSA 10 includes a sense amplifier 30 for amplifying sensed cardiac signals, a data processor 31 for processing the sensed signals, a pace processor 32 for generating atrial and/or ventricular pacing signals, an input/output interface circuit 33 for coupling the patient's heart 11 and implantable pacer 20 to the pacer system analyzer, and a control processor 34 for controlling the overall operation of the analyzer components. Control processor 34 is preferably microprocessor based and is programmed to generate system control voltages in response to user-entered keystroke commands from the user keyboard 24. Additionally, the control processor may generate a series of user instructions for display on LCD 25.

To facilitate measurement of patient parameters and to provide basic patient life support, pace processor 32 generates pacing pulses for application to heart 11. Atrial and ventricular pacing pulses of predetermined amplitude, duration and rate are generated in accordance with applied pace control signals from control processor 34. The pacing pulses are supplied from the pace processor through interface circuit 33 for application to the heart 11 through patient cable 13 and leads 14a and 14b.

As further illustrated in FIG. 2, implantable pacer 20 is connected through connector 21 to interface circuit 33. Upon application of an appropriate control signal from control processor 34 through a control bus 35, interface circuit 33 couples the patient cable 13 to pacer 20 whereupon the heart 11 is paced by the implantable pacer 20. Accordingly, the control processor can cause the heart to be paced by either pace processor 32 or implantable pacer 20.

Atrial and/or ventricular intracardiac signals detected by leads 14a and 14b are applied through cable 13 and interface 33 to respective inputs of sense amplifier 30. The sense amplifier generates atrial and/or ventricular strobe signals for application to control processor 34 through conductors 36 and 37 upon the occurrence of atrial or ventricular intracardiac signals above a predetermined sense threshold. The control processor sets the atrial and ventricular sense thresholds by applying digitally encoded instructions to the amplifier through data bus 38. Additionally, the sense amplifier provides amplified atrial and ventricular signals for application to data processor 31, and for application to EGM terminals 27 and 28 through an isolation circuit 40, as well as signals indicative of the peak atrial P-waves and ventricular R-waves sensed by leads 14a and 14b. Data processor 31 performs the mathematical operations required to calculate various patient, or pacer system, operating parameters for display on LCD 25 or for printing by printer/plotter 26.

Figure 3:
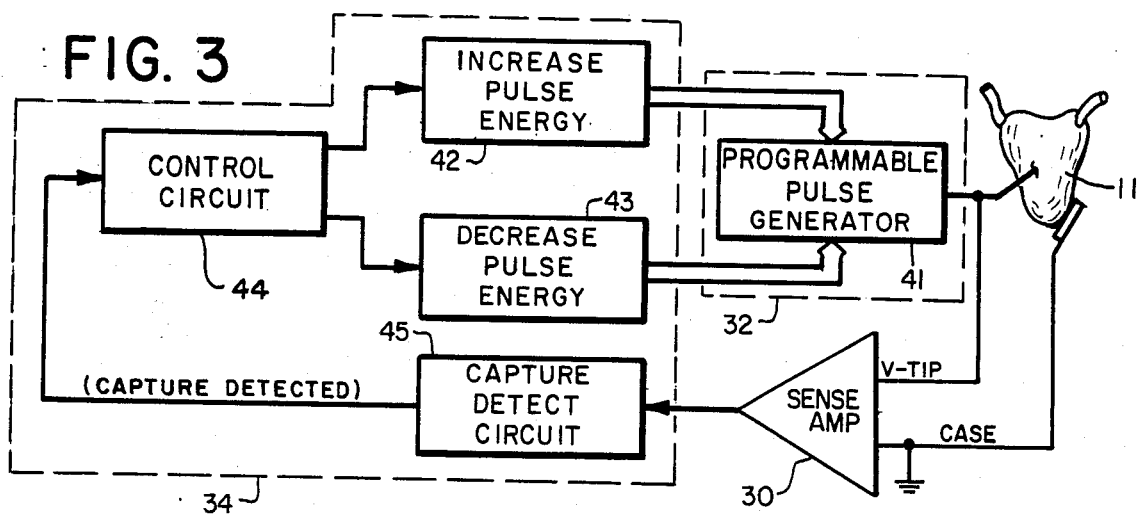
FIG. 3 is a simplified block diagram of the capture threshold determination system incorporated in the pacer system analyzer of FIG. 1.

Referring to FIG. 3, a basic automatic capture threshold determination system constructed in accordance with the present invention is illustrated. The output of a programmable pulse generator 41, which may comprise all or a part of the pace processor 32 of FIG. 2, is coupled through an appropriate lead to heart 11. For illustration, the ventricular unipolar lead set has been chosen. The energy of the pacing pulses generated by the programmable pulse generator may be increased or decreased as instructed by respective pulse energy control circuits 42 and 43. A third control circuit 44 develops appropriate control voltages for application to pulse energy control circuits 42 and 43 as required to increase or decrease the level of pacing pulses developed by pulse generator 41. Control circuit 44 and pulse level controls 42 and 43 may each comprise portions of control processor 34 and pace processor 32 (FIG. 2). Signals from the selected heart chamber are applied to the input of a capture detect system 45, which generally develops a "CAPTURE DETECTED" control voltage for application to control circuit 44 whenever a pacing pulse from generator 41 induces a contraction of heart 11.

In operation, the automatic capture threshold determination system systematically controls the energy of pacing pulses applied to the heart while simultaneously monitoring intracardiac electrical activity in order to detect the presence or absence of induced contractions. When such induced contractions are detected, capture is indicated and control circuit 44 decreases the amplitude of the applied pacing pulses. If capture is not indicated, the control circuit causes the pulse energy to increase until capture occurs. The servo-like process continues in a search mode until a condition is reached in which any incremental decrease in the pulse energy will result in less than 100% capture rate.

Figure 4:
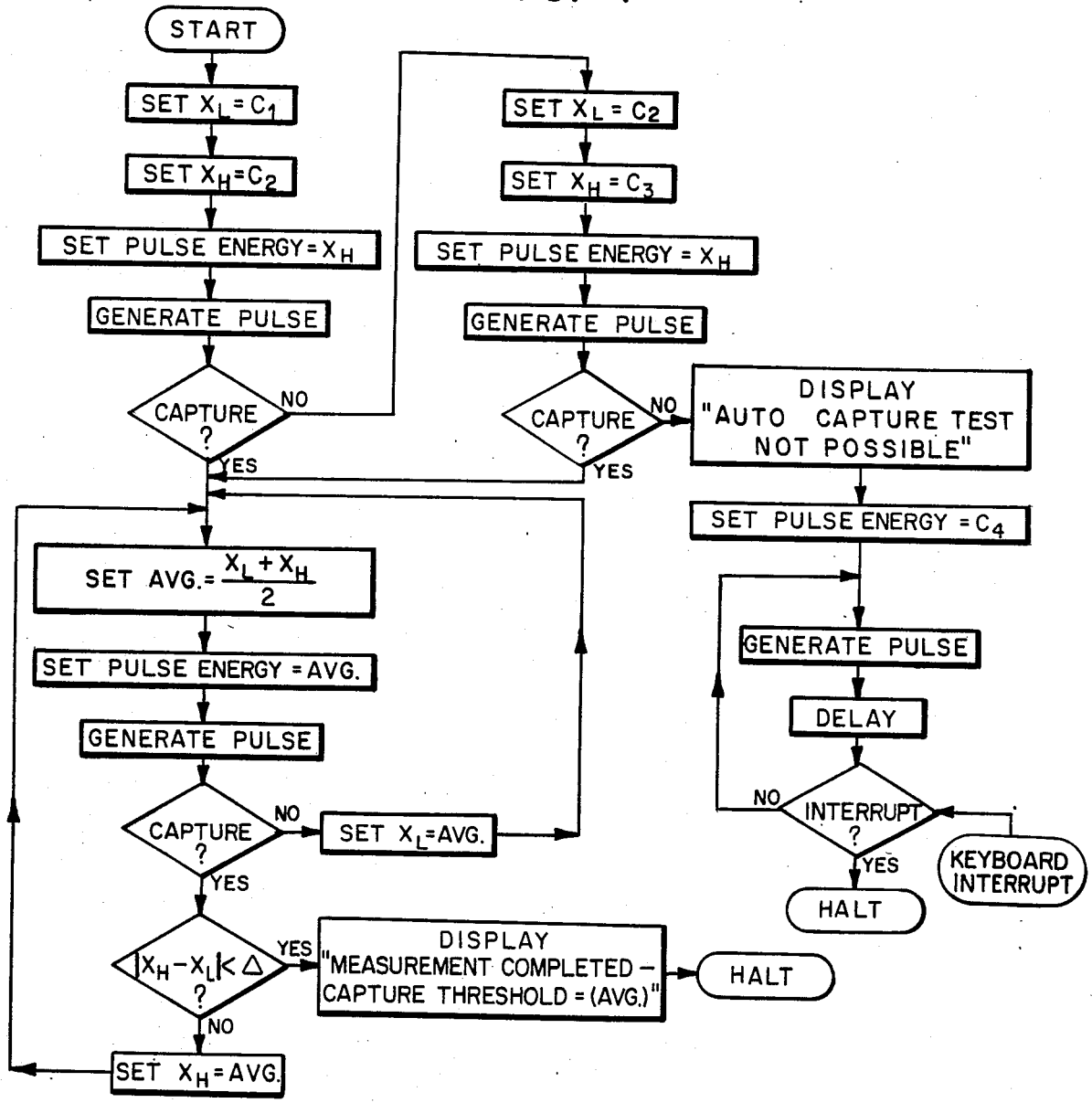
FIG. 4 is a flow diagram of steps performed by the capture threshold determination system useful in understanding the operation thereof.
Figure 5:
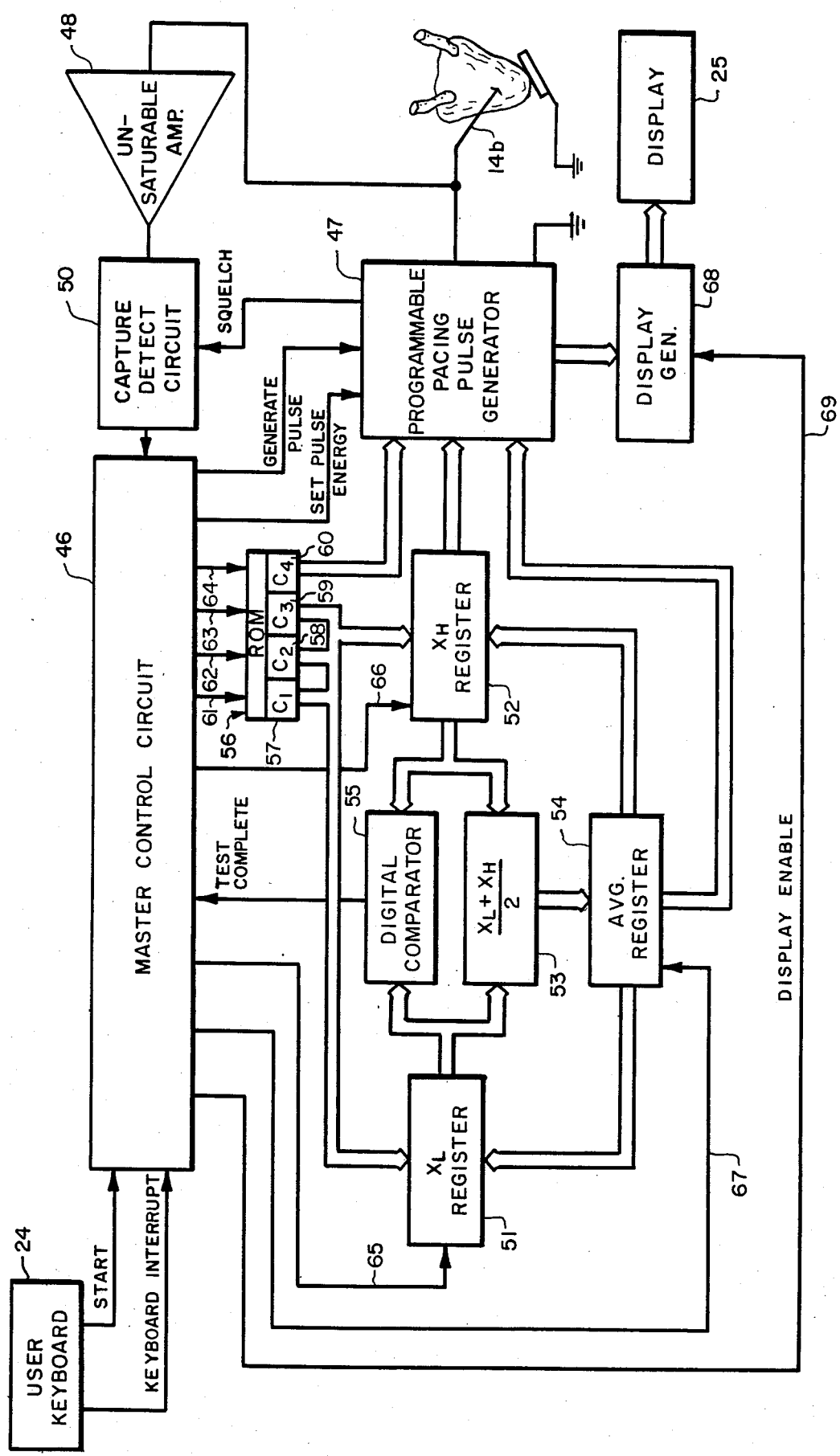
FIG. 5 is a functional block diagram of the capture threshold determination system incorporated in the pacer system analyzer of FIG. 1.

The operation of an actual system for implementing the automatic capture threshold determination system shown in FIG. 3 can be understood by reference to the flow diagram of FIG. 4 and the detailed system block diagram of FIG. 5. Referring to FIG. 5, the capture threshold determination system is seen to include a master control circuit 46 which controls the overall operation of the system in accordance with user-generated inputs from user keyboard 24. Additionally, the system includes a programmable pacing pulse generator 47, the output of which, in this example, is coupled to the ventricle of heart 11 through pacing lead 14b. It will be appreciated that the capture threshold determination system can be employed with both single and dual-chamber cardiac pacing as well as with unipolar and/or bipolar leads. Pacing pulse generator 47 generates a pacing pulse upon each application of a GENERATE PULSE control signal from master control circuit 46. Pulse energy is set in accordance with applied digitally encoded instructions upon application of a SET PULSE ENERGY control signal from the master control circuit.

The output of the programmable pulse generator 47 is coupled to the input of an unsaturable amplifier 48 such as that described in the copending application Ser. No. of the present inventor filed concurrently herewith, and entitled "Unsaturable Sense Amplifier for Pacer System Analyzer". The output of amplifier 48 is applied to the input of a capture detection circuit 50 such as that described in the copending application Ser. No. 738,607, of the present inventor filed concurrently herewith, and entitled "System and Method for Detecting Evoked Cardiac Contractions". Amplifier 48 remains sensitive during the immediate post-pulse lead recovery artifact period, while the capture detect circuit 50 returns a CAPTURE DETECT signal to master control circuit 46 in the event a cardiac contraction occurs during a predetermined period following each applied pacing pulse. As described in the aforementioned copending application Ser. No. 738,607, the master control circuit 46 and programmable pacing pulse generator 47 operate to develop paired pacing pulses for application to the heart.

To develop the digitally encoded instructions for setting the energy of the pacing pulses developed by programmable pulse generator 47, the capture threshold determination system includes a pair of data registers 51 and 52 which store a pair of variables $X_L$ and $X_H$, a digital averaging circuit 53 for computing the arithmetic average of variables $X_L$ and $X_H$, an "AVG" register 54 for storing the average so computed, and a digital comparator 55 for comparing the respective values of variables $X_L$ and $X_H$. The system further includes a read only memory (ROM) 56 having four memory locations 57-60 in which four constants $C_1$-$C_4$ are respectively stored. To retrieve constants $C_1$-$C_4$, the master control circuit 46 applies appropriate address signals to ROM 56 through address lines 61-64. The master control circuit also controls the input and output of data from registers 51, 52 and 54 by means of appropriate control signals applied through control lines 65, 66 and 67, respectively.

To develop appropriate user-viewable displays, the system further also includes a display generator 68 having an output coupled to LCD 25. The programmable pacing pulse generator 47 develops a digitally encoded representation of the then existing pulse energy, which is applied to the display generator 68. The display generator operates in accordance with commands from master control circuit 46 which are applied through control line 69.

Referring now to FIGS. 4 and 5, operation of the automatic threshold determination system begins when a START command from user keyboard 24 is applied to the master control circuit 46. Upon receiving the START command, the master control causes predetermined constant $C_1$ to be loaded into $X_L$ register 51 while constant $C_2$ is loaded into $X_H$ register 52. Variable $X_L$ represents a low pulse energy at which capture is not likely to take place, while variable $X_H$ represents an energy sufficiently high as to reliably result in capture. For convenience, constant $C_1$ may be selected to be near zero while constant $C_2$ represents a pulse amplitude at which capture is statistically likely to occur. It will be appreciated that, in order to save time, it may be desirable to set constant $C_1$ to some non-zero value.

Following such initialization of the $X_L$ and $X_H$ variables, the pulse energy of the programmable pacing pulse generator 47 is set to the energy value stored in register 52, or the amplitude then represented by variable $X_H$. Since, at this time, $X_H$ is equal to constant $C_2$, the initial pulse energy developed by the generator will correspond to the value of constant $C_2$. Next, the master control circuit instructs the pulse generator to apply a pacing pulse to the heart, after which the capture detect circuit 50 determines whether capture occurred.

In the event capture does not occur at the $C_2$ pulse energy, constant $C_2$ is loaded into the $X_L$ register 51 and a larger constant $C_3$ is loaded into the $X_H$ register 52. Next, the updated content of register 52 is loaded into pulse generator 47 with the result that the generator is set to produce pulses having an amplitude corresponding to constant $C_3$, either the maximum possible from the pulse generator, or an amplitude which has been statistically determined to be almost certain to result in capture. A pulse at the $C_3$ energy is then generated and applied to the heart. In the event the capture detect circuit 50 still fails to detect capture, the display "AUTO CAPTURE TEST NOT POSSIBLE" is generated on display 25 to alert the attending medical personnel, while the PSA reverts to operation in a basic life support or "STAT" mode.

In the STAT mode, the pulse energy is set to a still higher constant value $C_4$ which has been experimentally determined to virtually assure capture. After each pulse at the $C_4$ energy is generated, a check is made to determine whether a keyboard interrupt signal has been received. If not, the pulse generator simply continues generating pulses at a rate consistent with basic life support in order to assure the safety of the patient. In the event a keyboard interrupt signal is received, operation of the system in the STAT mode is halted.

In the event pulses at either the $C_2$ or $C_3$ levels result in capture, the pacing pulse energy is systematically decreased until a pulse amplitude, insufficient to cause cardiac capture, is reached. This is accomplished by loading the contents of $X_L$ and $X_H$ registers 51 and 52 into the averaging circuit 53 which calculates the arithmetic average of the then existing values of variables $X_L$ and $X_H$. The output of averaging circuit 53 is loaded into AVG register 54 to set a third variable "AVG" to the average level so computed. The content of the AVG register is then loaded into the programmable pacing pulse generator 47 whereupon a pulse at the AVG level is generated and the response of the heart noted.

In the event capture is not detected, the master control circuit causes the content of the AVG register 54 to be loaded into the $X_L$ register 51 with the result that variable $X_L$ will be set equal to the currently existing AVG value. A new average, using the now updated value of $X_L$, is then computed and loaded into the AVG register after which a pulse at the new AVG level is generated. In the event capture is still not detected, $X_L$ is once again updated to the current AVG value after which the average is once again recalculated. Since the average of $X_L$ and $X_H$ will always exceed $X_L$, the effect of each recalculation is that the pacing pulse energy will be progressively increased. This process continues until capture is detected.

In the event the AVG level is sufficient to cause cardiac capture, the pacing pulse amplitude will be reduced by loading the content of AVG register 54 into $X_H$ register 52 with the effect that variable $X_H$ will be set to the then existing value of variable AVG. The average is then recomputed using the new $X_H$ value and the updated result loaded into the AVG register 54. A pulse at the new AVG level is generated and the response of the heart noted. In the event capture still occurs, the pulse level is once again reduced in the same iterative manner.

Prior to setting $X_H$ equal to AVG, digital comparator 55 determines the difference between the respective values of $X_H$ and $X_L$. If $X_H$ and $X_L$ differ by less than a predetermined value ($\Delta$), it can be assumed that AVG will be substantially equal to the actual capture threshold. To enhance safety and reliability however, the final value of variable $X_H$ is preferably selected as the capture threshold. Accordingly, when the difference becomes less than $\Delta$, digital comparator 55 returns a "TEST COMPLETE" control signal to the master control circuit 46 whereupon the display "MEASUREMENT COMPLETED-CAPTURE THRESHOLD=$(X_H)$" is generated on LCD 25 and the system halted. Preferably, this occurs when the difference between $X_H$ and $X_L$ is no more than the minimum incremental pulse level change (i.e., the pulse amplitude resolution) available from the pacing pulse generator 47.

It will be observed that in general variable $X_H$ represents the minimum pulse amplitude at which capture has actually been detected, while variable $X_L$ represents the maximum pulse amplitude at which capture has not been detected. It will be apparent that as the system operates, the numerical value of variable $X_H$ will progressively decrease and the value of variable $X_L$ will progressively increase. Thus, the operation is such that $X_L$ and $X_H$ will at all times bracket and converge on the capture threshold. $X_H$ and $X_L$ continue converging in this manner until digital comparator 55 determines that the difference between $X_H$ and $X_L$ is less than the predetermined value, $\Delta$, whereupon the TEST COMPLETE signal is developed and applied to the master control circuit 46.

Since the capture detect circuit 50 responds to cardiac contractions which occur during a predetermined sampling period following the application of each pacing pulse, it is possible for a false capture indication to be made in the event a naturally occurring cardiac contraction occurs during the sampling period. To prevent system response to such false capture indications, the master control circuit 46, in accordance with one aspect of the invention, can be arranged to require the occurrence of a number of consecutive cardiac contractions, in response to a like number of consecutive applied pacing pulse pairs, before the existence of a valid capture condition is accepted. For example, since it is extremely improbable that three consecutive naturally occurring contractions will occur in synchrony with three consecutively applied pacing pulse pairs, the production of three consecutive CAPTURE DETECT signals from capture detect circuit 50 provides a highly reliable indication that the cardiac contractions are occurring in response to the applied pacing pulses. Accordingly, master control circuit 46 preferably requires the detection of three consecutive induced contractions before the existence of a valid capture condition is accepted.

This automatic capture threshold determination system permits rapid, accurate and automatic determination of a patient's capture threshold. It will be appreciated that while discrete system components, such as the various registers, the digital comparator, and the averaging circuit, have been presented and described, the system may be advantageously implemented using microprocessor-based circuitry in conjunction with suitable programming. Furthermore, it will be appreciated that the system provides flexibility for obtaining the most pertinent information concerning a patient's capture threshold. For example, the system can be easily adapted to vary the amplitude of pacing pulses while holding their duration constant, or in the alternative, can maintain amplitude constant while increasing or decreasing the pulse duration. This can be accomplished by loading the $X_L$ and $X_H$ registers with pulse duration instructions and instructing the pulse generator to set pulse duration in accordance with those instructions. Additionally, both the amplitude and duration of applied pacing pulses may be varied in accordance with a predetermined routine as required by a particular set of measurements, such as, for example, the compilation of the commonly accepted strength-duration data on an individual patient.

While a particular embodiment of the invention has been shown and described, it will be obvious to those skilled in the art that changes and modifications may be made therein without departing from the invention in its broader aspects, and, therefore, the aim in the appended claims is to cover all such changes and modifications as fall within the true spirit and scope of the invention.

I claim:

1. A capture threshold determination system for automatically determining the capture threshold energy level of applied pacing pulses required to reliably stimulate cardiac events in a patient heart, comprising:
   pulse generating means responsive to an applied energy level control signal for developing pacing pulses over a predetermined range of energy levels for application to the heart during successive reoccurring intervals;
   capture detection means for connection to the heart for detecting cardiac events stimulated during each successive itnerval in response to the pacing pulses generated during that interval, and providing a capture detection signal indicative thereof;
   first register means for storing a lower limit pulse energy level and providing an output indicative thereof;
   second register means for storing an upper limit pulse energy level and providing an output indicative thereof;
   computing means coupled to and responsive to the outputs of said first and second register means for computing the average of said pulse energy levels stored in said first and second register means and providing an output indicative thereof;
   pulse amplitude control means coupled to and responsive during an initial one of said intervals to the output of one of said register means, and during subsequent intervals coupled to and responsive to the output of said computing means for producing an energy level control signal for application to said pulse generating means to cause said generating means to produce pacing pulses at the energy level of said one register during said initial interval, and at the average energy levels computed by said computing means during subsequent intervals;
   transfer means responsive to said capture detection signal upon completion of each interval for transferring the then existing average pulse energy level indicated by the output of said computing means to said first register means in the event of non-capture during that interval, and to said second register means in the event of capture during that interval, whereby the energy level of said pacing pulses as determined by said energy level control signal approaches the capture threshold level with successive intervals; and
   output circuit means coupled to and responsive to the outputs of said register means for providing an output control signal upon the difference between said outputs falling below a predetermined threshold level to indicate generation of pacing pulses at the capture threshold level.

2. A capture threshold determination system as defined in claim 1 wherein said output control signal is applied to said transfer means to inhibit said transfer means from responding to said capture detection signal and thereby prevent the occurrence of further intervals.

3. A capture threshold determination system as defined in claim 1 wherein siad output circuit means further provide an output data signal indicative of the energy level of said pacing pulses generated by said pulse generating means upon said outputs of said register means falling below said predetermined threshold level.

4. A capture threshold determination system as defined in claim 3 wherein said output circuit means are coupled to and provide an output data signal indicative of the output of said second register means.

5. A capture threshold determination system for automatically determining the capture threshold energy level of applied pacing pulses required to reliably stimulate cardiac events in a patient heart, comprising:
   pulse generating means responsive to an applied energy level control signal for developing pacing pulses over a predetermined range of energy levels for application to the heart during successive reoccurring intervals;
   capture detection means for connection to the heart for detecting cardiac events stimulated during each successive interval in response to the pacing pulses generated during that interval, and providing a capture detection signal indicative thereof;
   pulse amplitude control means for producing an energy level control signal for application to said pulse generating means, said generating means being operable to generate during an initial interval pacing pulses at either an upper limit greater than the threshold level, or at a lower limit less than the threshold level and being further operable during subsequent;
   intervals to generate pacing pulses at an energy level corresponding to either the average between a new upper limit corresponding to the average between the upper and lower limits of the previous interval and the lower limit of the previous interval upon detection of a cardiac event, or to the average between a new lower limit corresponding to the average between the upper and lower limits of the previous intervals and the upper limit of the previous interval upon non-detection of a cardiac event, whereby the energy level of said pacing pulses with subsequent intervals approaches said threshold level; and
   output circuit means coupled to said pulse amplitude control means and responsive to said upper and lower limits for providing an output control signal indicative of generation of pacing pulses at the threshold level upon the difference between said limits falling below a predetermined threshold level.

6. A capture threshold determination systen as defined in claim 5 wherein said output control signal is applied to said pulse amplitude control means to inhibit further change in said energy level control signal.

7. A capture threshold determination system as defined in claim 5 wherein said output circuit means further provide an output data signal indicative of the energy level of said pacing pulses generated by said pulse generating means upon said outputs of said register meaos falling below said predetermined threshold level.

8. The method of automatically determining the threshold energy level of applied pacing pulses required to reliably stimulate cardiac events in a patient heart, comprising:
- developing in response to an applied energy level control signal pacing pulses at predetermined energy levels for application to the heart during successive reoccurring intervals;
- applying the pacing pulses to the patient heart;
- detecting cardiac events stimulated during each successive interval in response to the pacing pulses generated during that interval, and providing a capture detection signal indicative thereof;
- storing a lower limit pulse energy level in first register means;
- storing an upper limit pulse energy level in second register means;
- computing an average pulse energy level from the average of said pulse energy levels stored in said first and second register means;
- producing an energy level control signal during an initial one of the intervals corresponding to one of said register means to cause said pacing pulses to be produced at the pulse energy level stored therein;
- transferring during each subsequent interval the computed average energy level of the previous interval said first register means in the event of non-capture during that interval, and to said second register means in the event of non-capture during that interval, recomputing the average pulse energy level from the pulse energy levels then stored in said first and second register means, and producing an energy level control signal corresponding to said computed average pulse energy level, whereby during subsequent intervals the energy levels of said pacing pulses approaches the capture threshold level; and
- providing in response to the difference between the energy levels in said registers falling below a predetermined threshold level an output control signal indicative of detection of the capture threshold level.

9. The method of capture threshold determination defined in claim 8 including the additional step of providing an output data signal indicative of the energy level of said pacing pulse as the capture threshold level.

10. The method of automatically determining the threshold energy level of applied pacing pulses required to reliably stimulate cardiac events in a patient heart, comprising:
- developing in response to an applied energy level control signal pacing pulses at predetermined energy levels for application to the heart during successive reoccurring intervals;
- applying the pacing pulses to the patient heart;
- detecting cardiac events stimulated during each successive interval in response to the pacing pulses generated during that interval, and providing a capture detection signal indicative thereof;
- producing an energy level control signal to cause the generation during an initial interval of paciog pulses at either an upper limit greater than the threshold level, or at a lower limit less than the threshold level;
- producing an energy level control signal during subsequent intervals to cause the generation of pacing pulses at an average energy level corresponding to either the average between a new upper limit corresponding to the average between the upper and lower limits of the previous interval and the lower limit of the previous interval upon detection of a cardiac event, or to the average between a new lower limit corresponding to the average between the upper and lower limits of the previous interval and the upper limit of the previous interval upon non-detection of a cardiac event, whereby the energy level of said pacing pulses approaches said threshold level with successive intervals;
- determining the difference between said upper and lower limits; and
- providing in response to said difference falling below a predetermined threshold level an output control signal indicative of detection of the threshold level.

11. The method of capture threshold determination defined in claim 10 including the additional step of providing an output data signal indicative of the energy level of said pacing pulse as the capture threshold level.

* * * * *